(12) United States Patent
Kano

(10) Patent No.: US 11,202,608 B2
(45) Date of Patent: Dec. 21, 2021

(54) RADIOGRAPHY APPARATUS

(71) Applicant: FUJIFILM Corporation, Tokyo (JP)

(72) Inventor: Shinichi Kano, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/029,134

(22) Filed: Sep. 23, 2020

(65) Prior Publication Data

US 2021/0093263 A1    Apr. 1, 2021

(30) Foreign Application Priority Data

Sep. 30, 2019   (JP) .............................. JP2019-180293

(51) Int. Cl.
*A61B 6/08*   (2006.01)
*A61B 6/00*   (2006.01)

(52) U.S. Cl.
CPC .............. *A61B 6/08* (2013.01); *A61B 6/4233* (2013.01); *A61B 6/4441* (2013.01)

(58) Field of Classification Search
CPC ......... A61B 6/032; A61B 6/4452; A61B 6/54; A61B 2034/2068; A61B 2034/107; A61B 2034/2055; A61B 2090/0807; A61B 2090/308; A61B 2090/309
See application file for complete search history.

(56) References Cited

U.S. PATENT DOCUMENTS

2017/0156800 A1 *   6/2017   Brown ................. A61B 6/4441

FOREIGN PATENT DOCUMENTS

WO       2014/148266 A1     9/2014

* cited by examiner

*Primary Examiner* — Don K Wong
(74) *Attorney, Agent, or Firm* — Studebaker & Brackett PC

(57) ABSTRACT

A radiography apparatus includes: an irradiation unit that emits radiation; an arm to which the irradiation unit and an image receiving unit that receives the radiation are capable of being attached at a position where the irradiation unit and the image receiving unit face each other with a subject interposed therebetween and which is rotated to reverse a positional relationship between the irradiation unit and the image receiving unit with respect to the subject; a first light source that is provided in the irradiation unit and emits visible light indicating an irradiation field of the radiation; and a second light source that is provided in the image receiving unit and emits visible light indicating a center position of the irradiation field of the radiation emitted by the irradiation unit.

10 Claims, 15 Drawing Sheets

RADIOGRAPHY APPARATUS

CROSS-REFERENCE TO RELATED APPLICATIONS

The present application claims priority under 35 U.S.C. § 119 to Japanese Patent Application No., 2019-180293 filed on Sep. 30, 2019. The above application is hereby expressly incorporated by reference, in its entirety, into the present application.

BACKGROUND

1. Technical Field

The present disclosure relates to a radiography apparatus.

2. Description of the Related Art

WO2014/148266A discloses an X-ray imaging apparatus in which an X-ray source (irradiation unit) and an X-ray detector (image receiving unit) are mounted on an arm curved in a C-shape. The X-ray imaging apparatus disclosed in WO2014/148266A rotates the arm to move the X-ray source in any direction on the up, down, left, or right sides of a subject while maintaining a facing relationship between the X-ray source and the X-ray detector. Therefore, the X-ray imaging apparatus disclosed in WO2014/148266A can respond to both a so-called overtube imaging method in which the X-ray source is disposed above the subject and the X-ray detector is disposed below the subject for imaging and a so-called undertube imaging method in which the X-ray source is disposed below the subject and the X-ray detector is disposed above the subject for imaging.

Further, in the X-ray imaging apparatus disclosed in WO2014/148266A, each of the X-ray source and the X-ray detector is provided with an irradiation range display unit that emits visible light indicating the irradiation range of the X-ray source. A second irradiation range display unit provided in the X-ray source comprises a light source that is provided in a collimator of the X-ray source. The light source emits light to the subject through an irradiation opening of the collimator. Therefore, the irradiation range corresponding to the irradiation opening is displayed on the subject.

In addition, a first irradiation range display unit provided in the X-ray detector comprises a laser light source and the periphery of the irradiation field of the X-ray source is displayed by the laser light source.

Therefore, in the X-ray imaging apparatus disclosed in WO2014/148266A, even in a case in which imaging is performed by the undertube method in which the X-ray source is disposed below the subject, the irradiation field of the X-ray source can be displayed by the first irradiation range display unit since the first irradiation range display unit is provided in the X-ray detector disposed above the subject.

SUMMARY

In many cases, the undertube method is used to capture a moving image during surgery. However, the irradiation field is rarely displayed by visible light during surgery. The main purpose of displaying the irradiation field using visible light is to check the irradiation field without emitting radiation in order to appropriately set the irradiation field to a treatment target part to be subjected to surgery. In addition, in a case in which a treatment of puncturing the treatment target part with a needle or a treatment of inserting a thin tube, such as a catheter, into the treatment target part is performed, the area of the treatment target part may be very small.

In consideration of these circumstances, the X-ray imaging apparatus disclosed in WO2014/148266A has the following problems. That is, the first irradiation range display unit disclosed in WO2014/148266A is a type which indicates the periphery of the irradiation field with linear laser light. In a case in which the irradiation field is appropriately set with respect to a central region of the treatment target part, it is difficult to see the center position of the irradiation field at a glance even in the method that linearly indicates the periphery of the irradiation field with laser light. In particular, in a case in which the area of the treatment target part is very small with respect to the area of the irradiation field whose periphery is linearly indicated, the distance between the periphery of the irradiation field and the center position of the irradiation field is long. Therefore, it is difficult to estimate the center position from the periphery and to align the center position of the irradiation field with the center position of the treatment target part. In a case in which the center position of the irradiation field is not aligned with the center position of the treatment target part and the size of the irradiation opening is adjusted to narrow the irradiation field, there is a concern that the treatment target part will deviate from the irradiation field.

In addition, an irradiation surface irradiated with light, such as the body surface of the subject or the outer surface of a sheet covering the subject during surgery, is not flat and has undulations. In a case in which the irradiation surface has undulations, linear light that indicates the periphery of the irradiation field is curved following the undulations on the irradiation surface. Therefore, the light is not displayed linearly. This is also one of the reasons why the method of displaying the periphery of the irradiation field makes it difficult to understand the center position of the irradiation field.

An object of the technology of the present disclosure is to provide a radiography apparatus that can appropriately indicate an irradiation field in an overtube method and enables an operator to easily understand a center position of the irradiation field before radiation is emitted, as compared to the related art, even in a case in which imaging is performed by an undertube method.

According to a first aspect of the present disclosure, there is provided a radiography apparatus comprising: an irradiation unit that emits radiation; an arm to which the irradiation unit and an image receiving unit that receives the radiation are capable of being attached at a position where the irradiation unit and the image receiving unit face each other with a subject interposed therebetween and which is rotated to reverse a positional relationship between the irradiation unit and the image receiving unit with respect to the subject; a first light source that is provided in the irradiation unit and emits visible light indicating an irradiation field of the radiation; and a second light source that is provided in the image receiving unit and emits visible light indicating a center position of the irradiation field of the radiation emitted by the irradiation unit.

According to the radiography apparatus of the first aspect, the arm is rotated to move the positional relationship between the image receiving unit and the irradiation unit that face each other with the subject interposed therebetween. Therefore, it is possible to emit radiation in a state in which the irradiation unit is disposed on the upper side and the image receiving unit is disposed on the lower side with the subject interposed between (undertube method).

Further, the image receiving unit comprises the second light source that emits visible light indicating the center position of the irradiation field of the radiation emitted by the irradiation unit. Therefore, it is easy to understand the center position of the irradiation field before radiation is emitted, as compared to the related art that visible light indicating the periphery of the irradiation field is emitted, even in a case in which imaging is performed by the undertube method.

According to a second aspect of the present disclosure, in the radiography apparatus according to the first aspect, the irradiation unit may continuously emit the radiation to capture a moving image.

As described in Summary, in a case in which a moving image is captured, the necessity for indicating the center position of the irradiation field is particularly higher than that in a case in which a still image is captured. In the radiography apparatus according to the second aspect, the image receiving unit comprises the second light source. Therefore, it is possible to indicate the center position of the irradiation field in a case in which a moving image is captured.

According to the third aspect of the present disclosure, in the radiography apparatus according to the first aspect or the second aspect, the second light source may be a laser light source.

In the radiography apparatus according to the third aspect, the second light source is a laser light source. The laser light sources have a narrower divergence angle and higher directivity than other light sources such as LED light sources and halogen lamps. Therefore, it is easy for the laser light source to emit light indicating one point and linear or planar light and the laser light source is suitable as a light source for displaying the center position of the irradiation field.

According to a fourth aspect of the present disclosure, in the radiography apparatus according to any one of the first to third aspects, the second light source may form, as the visible light, a plurality of beams that linearly illuminate a surface of the subject and intersect each other on the surface and the center position of the irradiation field may be indicated by an intersection point of the plurality of beams.

In the radiography apparatus according to the fourth aspect, it is possible to indicate the center position of the irradiation field at the intersection point of the lines that extend linearly on the surface of the subject. Therefore, it is easy for the operator of the radiography apparatus to clearly visually recognize the center position. Further, this configuration is particularly effective in a case in which the surface of the subject has undulations.

According to a fifth aspect of the present disclosure, in the radiography apparatus according to any one of the first to fourth aspects, the first light source may be an LED light source.

In the radiography apparatus according to the fifth aspect, the first light source is an LED light source. The LED light source can be downsized as compared to, for example, a halogen lamp. Further, since the divergence angle is larger than that of the laser light source, the LED light source is suitable as a light source for illuminating the entire region of the irradiation field.

According to a sixth aspect of the present disclosure, in the radiography apparatus according to any one of the first to fifth aspects, at least one of the first light source or the second light source is a color-variable light source that is capable of changing a color.

According to the radiography apparatus of the sixth aspect, at least one of the first light source and the second light source may change the color. The color is changed to a color that is highly visible to the user of the radiography apparatus.

According to a seventh aspect of the present disclosure, in the radiography apparatus according to the sixth aspect, the color-variable light source may have a plurality of light emitting elements that emit light components of different colors.

In the radiography apparatus according to the seventh aspect, the color-variable light source has a plurality of light emitting elements that emit light components of different colors. Therefore, the range of colors that can be changed is wider than that in a case in which only a single-color light emitting element is provided.

According to an eighth aspect of the present disclosure, the radiography apparatus according to the sixth or seventh aspect may further comprise a color sensor that detects a color of the subject; and a color adjustment unit that adjusts a color of the light emitted by the color-variable light source according to the color detected by the color sensor.

In the radiography apparatus according to the eighth aspect, the color adjustment unit adjusts the color of light according to the color of the subject detected by the color sensor. Therefore, it is possible to easily change the color.

According to a ninth aspect of the present disclosure, the radiography apparatus according to any one of the first to eighth aspects may further comprise a light amount adjustment unit that adjusts an amount of light of at least one of the first light source or the second light source.

In the radiography apparatus according to the ninth aspect, the light amount adjustment unit adjusts the amount of light. Therefore, it is possible to adjust the amount of light such that light visibility is high.

According to a tenth aspect of the present disclosure, the radiography apparatus according to the ninth aspect may further comprise an illuminance sensor that detects environmental illuminance The light amount adjustment unit may adjust an amount of visible light indicating the irradiation field according to the illuminance detected by the illuminance sensor.

In the radiography apparatus according to the tenth aspect, the light amount adjustment unit adjusts the amount of visible light indicating the irradiation field according to the illuminance detected by the illuminance sensor. Therefore, it is possible to adjust the amount of light according to the environmental illuminance such that visibility is high.

According to the present disclosure, it is possible to provide the radiography apparatus that can appropriately indicate the irradiation field in the overtube method and enables the operator to easily understand the center position of the irradiation field before radiation is emitted, as compared to the related art, even in a case in which imaging is performed by the undertube method.

BRIEF DESCRIPTION OF THE DRAWINGS

Exemplary embodiments according to the technique of the present disclosure will be described in detail based on the following figures, wherein.

DETAILED DESCRIPTION

Figure 1:
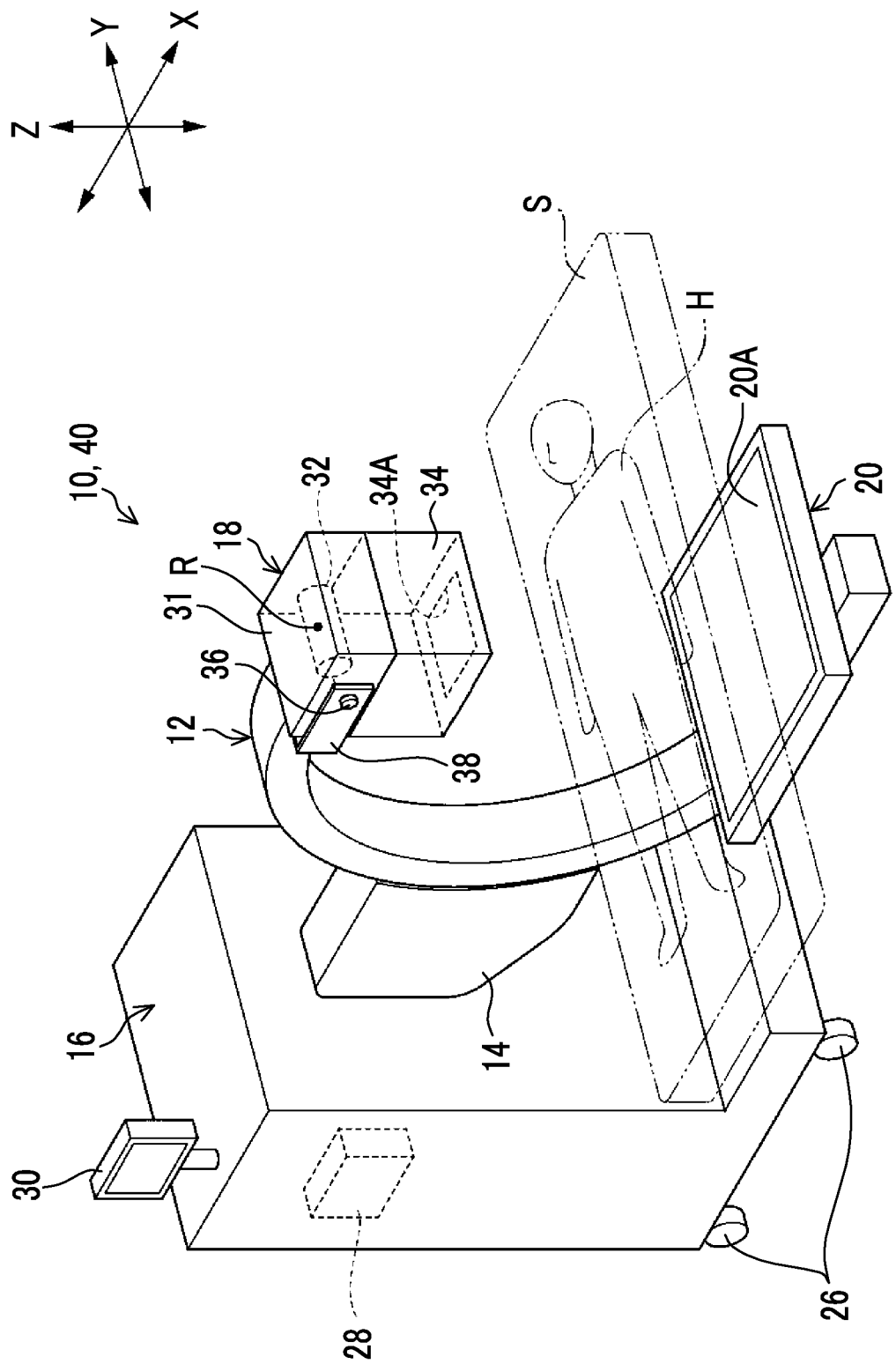
FIG. 1 is an overall perspective view illustrating a radiography apparatus according to a first embodiment.

Hereinafter, radiography apparatuses according to first to third embodiments of the present disclosure will be sequentially described with reference to the drawings. In the drawings, an arrow X indicates the front-rear direction of the radiography apparatus, an arrow Y indicates the width direction of the radiography apparatus, and an arrow Z indicates the vertical direction.

First Embodiment

First, a radiography apparatus according to the first embodiment of the present disclosure will be described with reference to FIGS. 1 to 11.

Overall Configuration of Radiography Apparatus

A radiography apparatus 10 according to this embodiment illustrated in FIG. 1 is an apparatus that captures a radiographic image of a subject H. The radiography apparatus 10 can capture, for example, moving images and still images of the subject H. The capture of the moving image is performed, for example, in a case in which a treatment target part of the subject H is displayed as a moving image during surgery (also referred to as fluoroscopy). In the capture of the moving image, for example, the moving image of the subject H is displayed on a monitor (not illustrated) that is provided separately from the radiography apparatus 10. Of course, data of the captured moving image may be stored in a memory of the radiography apparatus 10. In addition, in the case of the capture of the still image, the captured still image may be displayed on the monitor or may be stored in the memory of the radiography apparatus 10.

As illustrated in FIG. 1, the radiography apparatus 10 includes an arm 12 (referred to as a C-arm or the like) having a C-shape (an arc shape) in a side view and a main body 16 to which a support portion 14 is attached. In the following description, it is assumed that the side of the radiography apparatus 10 on which the arm 12 is provided is the front side of the radiography apparatus 10 and the side of the radiography apparatus 10 on which the main body 16 is provided is the rear side of the radiography apparatus 10.

Configuration of Arm

The arm 12 has two ends. An irradiation unit 18 is provided at one end of the arm 12 and an image receiving unit 20 is provided at the other end. The arm 12 can hold the irradiation unit 18 and the image receiving unit 20 in a posture in which they face each other.

A space, into which the subject H and a bed S on which the subject H lies supine can be inserted, is ensured between the irradiation unit 18 and the image receiving unit 20. That is, the image receiving unit 20 that receives radiation and the irradiation unit 18 can be attached to the arm 12 at a position where they face each other with the subject H interposed therebetween. In the following description, in some cases, in a side view of the arm 12 (as viewed from the Y direction in FIG. 1), a direction in which the irradiation unit 18 and the image receiving unit 20 are provided is referred to as the front side of the arm 12 and the side of the support portion 14 is referred to as the rear side of the arm 12.

Figure 2A:
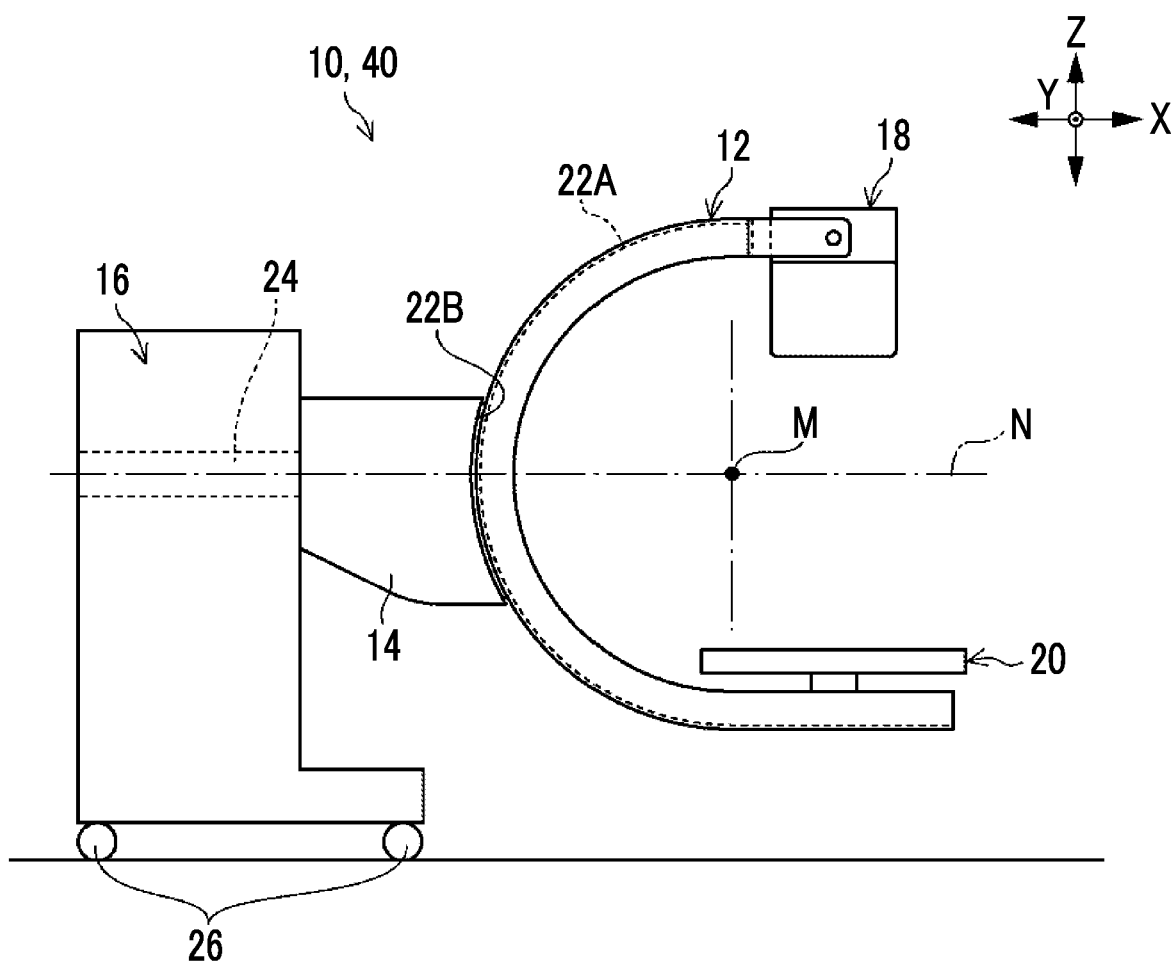
FIG. 2A is a side view illustrating the radiography apparatus according to the first embodiment.

Further, as illustrated in FIG. 2A, the arm 12 can be rotated about at least two different axis lines M (an axis line parallel to the Y axis) and N (an axis line parallel to the X axis) with respect to the main body 16. Specifically, a rail 22B is formed in the support portion 14. A rail fitting portion 22A that is fitted to the rail 22B is provided in an outer peripheral surface of the arm 12. The rail 22B has, for example, a groove shape and the rail fitting portion 22A having a convex shape is fitted to the rail 22B. The rail fitting portion 22A has an arc shape following the shape of the arm 12. The rail 22B also has an arc shape that has the same radius as the arc of the arm 12.

The rail fitting portion 22A formed on the arm 12 slides along the rail 22B formed on the support portion 14 such that the arm 12 can be orbitally rotated about the axis line M at the center of the arc of the arm 12 with respect to the support portion 14 and the main body 16.

Figure 2B:
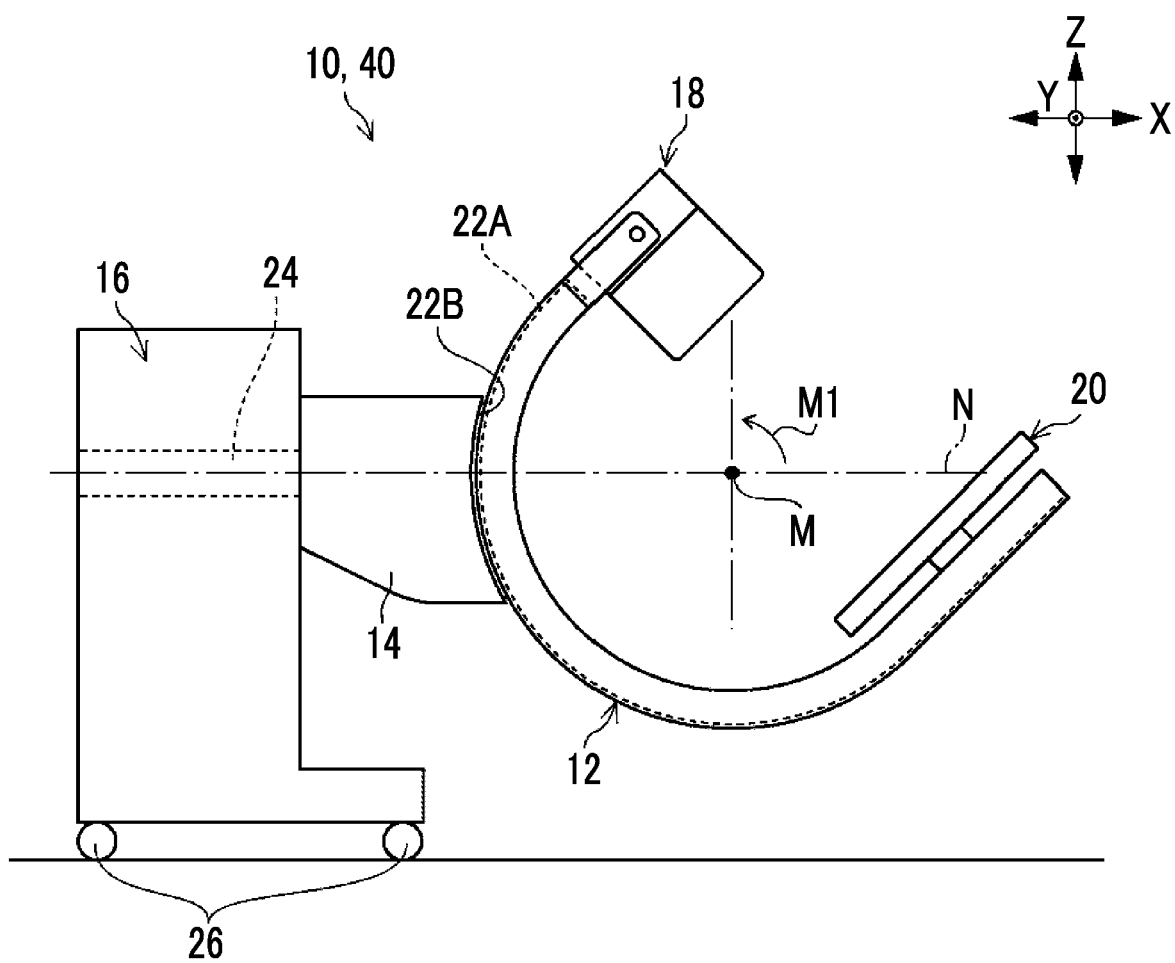
FIG. 2B is a side view illustrating a state in which an arm of the radiography apparatus illustrated in FIG. 2A is rotated in the direction of an arrow M1.
Figure 2C:
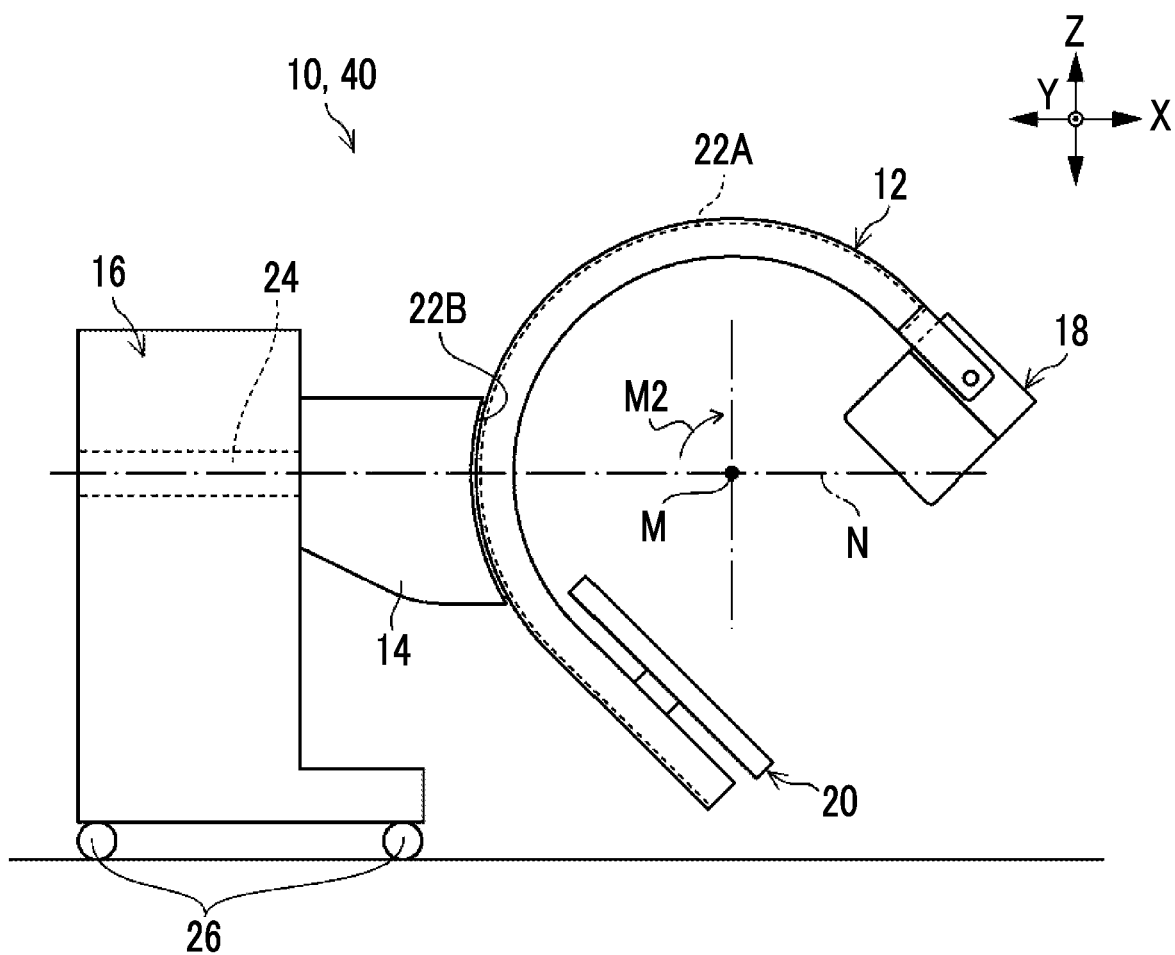
FIG. 2C is a side view illustrating a state in which the arm of the radiography apparatus illustrated in FIG. 2A is rotated in the direction of an arrow M2.

That is, as illustrated in FIGS. 2B and 2C, it is possible to orbitally rotate the arm 12 about the axis line M in the direction of an arrow M1 (counterclockwise in FIG. 2B) and the direction of an arrow M2 (clockwise in FIG. 2C). Therefore, it is possible to rotate the irradiation unit 18 and the image receiving unit 20 provided at both ends of the arm 12 about the body axis (an axis parallel to the Y axis) of the subject H (see FIG. 1).

The support portion 14 has a support shaft 24 that extends in the front-rear direction of the radiography apparatus 10 and the support shaft 24 is supported by the main body 16 through a bearing (not illustrated). Therefore, as illustrated in FIGS. 3A to 3C, the support portion 14 can be rotated about the axis line N of the support shaft 24 as a rotation center with respect to the main body 16 and the arm 12 can also be rotated about the axis line with respect to the main body 16 together with the support portion 14.

Figure 3A:
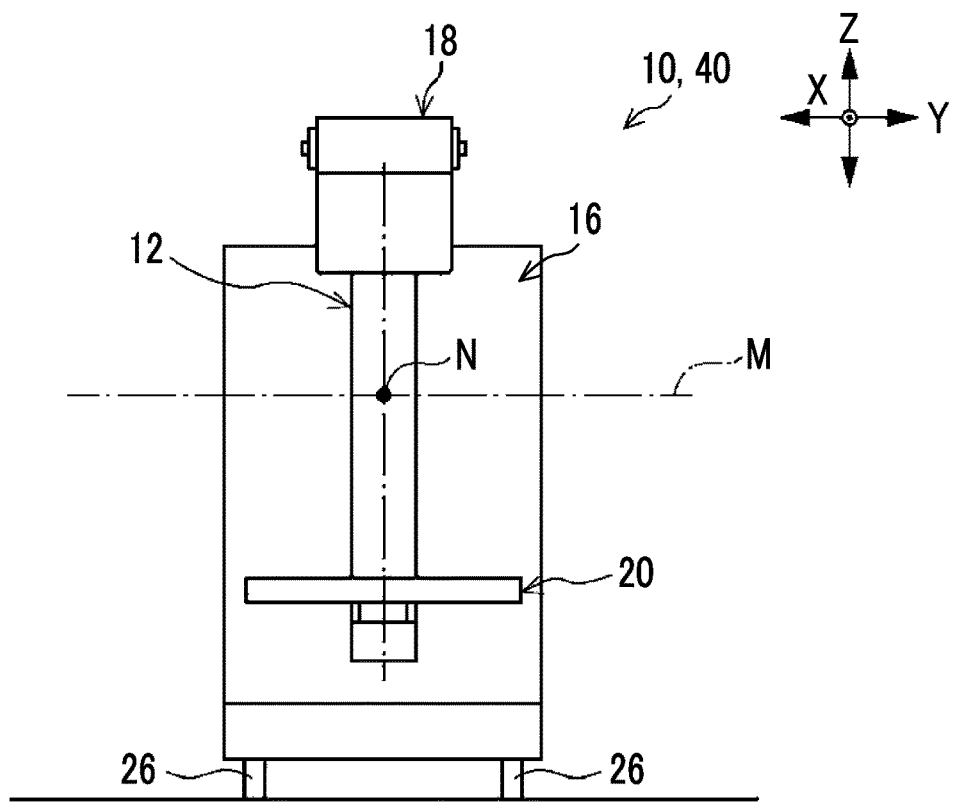
FIG. 3A is a front view illustrating the radiography apparatus according to the first embodiment.
Figure 3B:
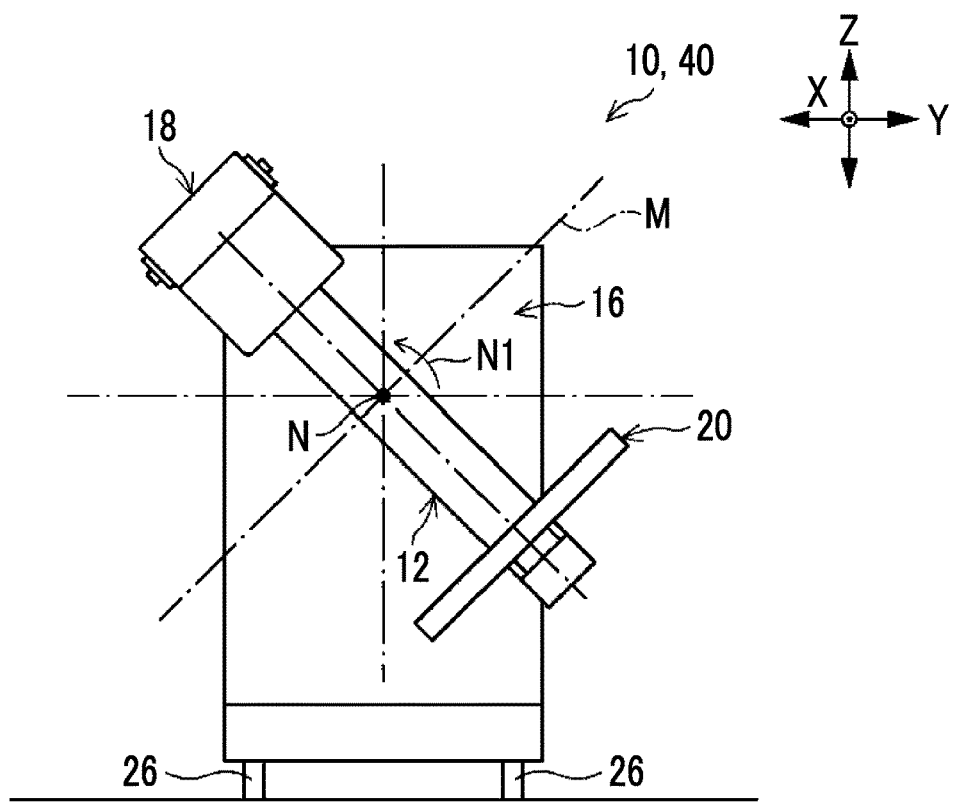
FIG. 3B is a side view illustrating a state in which the arm of the radiography apparatus illustrated in FIG. 3A is rotated in the direction of an arrow N1.
Figure 3C:
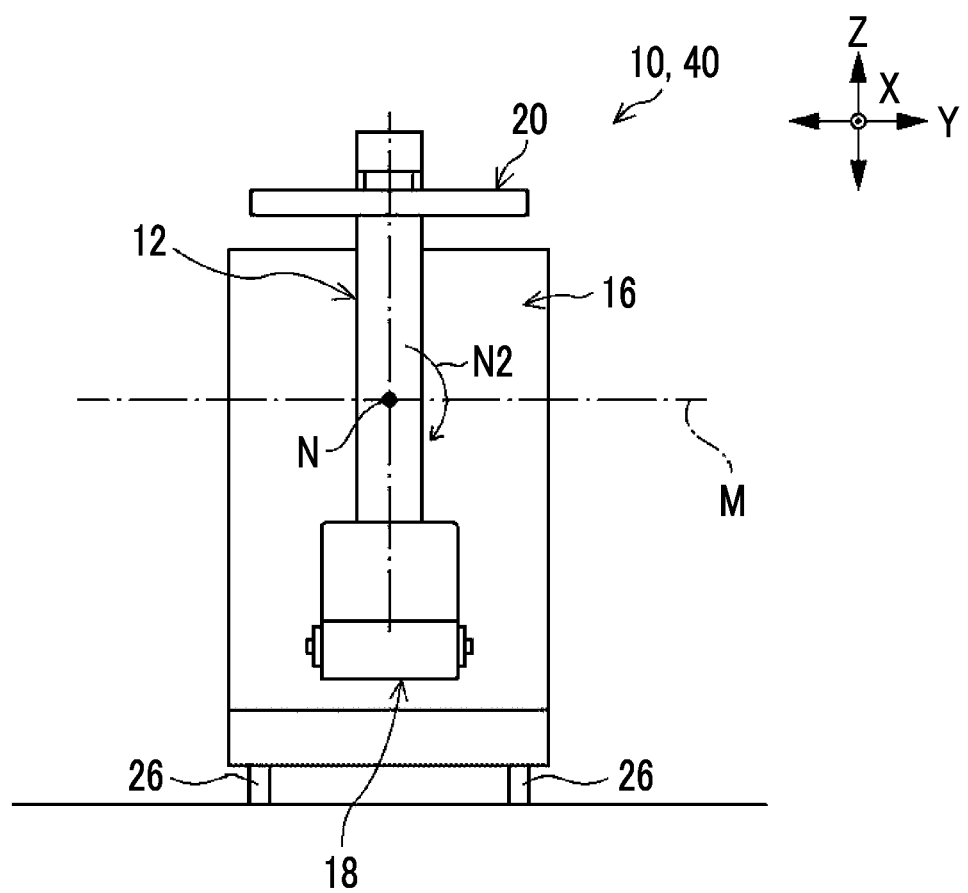
FIG. 3C is a side view illustrating a state in which the arm of the radiography apparatus illustrated in FIG. 3A is rotated 180° in the direction of an arrow N2.

That is, as illustrated in FIGS. 3B and 3C, it is possible to rotate the arm 12 about the axis line N in the direction of an arrow N1 (counterclockwise in FIG. 3B) and the direction of an arrow N2 (clockwise in FIG. 3C). Therefore, it is possible to reverse the positions of the irradiation unit 18 and the image receiving unit 20 provided at both ends of the arm 12 with respect to the subject H (see FIG. 1) in the vertical direction (Z-axis direction). In other words, the arm 12 can be rotated to reverse the positional relationship between the irradiation unit 18 and the image receiving unit 20 with respect to the subject H.

Here, the posture of the arm 12 in which the irradiation unit 18 is disposed above the image receiving unit 20 as illustrated in FIG. 3A is also referred to as an overtube posture since a radiation tube 32 (see FIG. 1) included in the irradiation unit 18 is located above the subject H. In contrast, the posture of the arm 12 in which the irradiation unit 18 is disposed below the image receiving unit 20 illustrated in FIG. 3C is referred to as an undertube posture since the radiation tube 32 is located below the subject H. Hereinafter, an imaging method in a state in which the arm 12 is in the overtube posture is referred to as an overtube method and an imaging method in a state in which the arm 12 is in the undertube posture is referred to as an undertube method.

In the overtube method, it is possible to increase a distance between the irradiation unit 18 and the subject H (see FIG. 1) and thus to capture an image of a relatively wide region, as compared to the undertube method. Therefore, the overtube method is mainly used to capture the still image of the subject H. In contrast, in the undertube method, since the radiation emitted from the irradiation unit 18 is partially shielded by, for example, the bed S, it is possible to reduce the amount of radiation exposure of a surgeon or an operator (not illustrated) around the subject H (see FIG. 1). Therefore, the undertube method is used for the capture of the moving image of the subject H in which radiation is continuously emitted.

Configuration of Main Body

As illustrated in FIG. 1, a plurality of casters 26 are attached to a lower portion of the main body 16 of the radiography apparatus 10 and the operator can push the radiography apparatus 10 with hands to move the radiography apparatus 10 into, for example, an operating room or a hospital ward. That is, the radiography apparatus 10 according to this embodiment is a mobile type.

Further, the main body 16 includes a control device 28 that controls each unit of the radiography apparatus 10, such as the irradiation unit 18, and an operation panel 30 that is, for example, a touch panel type. The configuration of the control device 28 will be described in detail below.

The operation panel 30 functions as an operation unit that inputs an operation command to each unit of the radiography apparatus 10, such as the irradiation unit 18, to operate each unit and a display unit that displays various kinds of information, such as a warning message and a radiographic image output from the image receiving unit 20. In addition, the main body 16 comprises various switches (not illustrated) including, for example, a power switch of the radiography apparatus 10, a power supply circuit that supplies power to each unit of the radiography apparatus 10, and a battery.

Configuration of Irradiation Unit

The irradiation unit 18 has the radiation tube 32 that generates radiation from a focus position R and emits the radiation. Specifically, the irradiation unit 18 comprises a radiation source 31 and an irradiation field limiter 34. The radiation source 31 comprises the radiation tube 32 that generates radiation. The radiation is, for example, X-rays. The radiation tube 32 generates radiation by colliding electrons generated from a cathode with a target (anode). The position where the electrons collide with the target is the focus position R where radiation is emitted.

Figure 4:
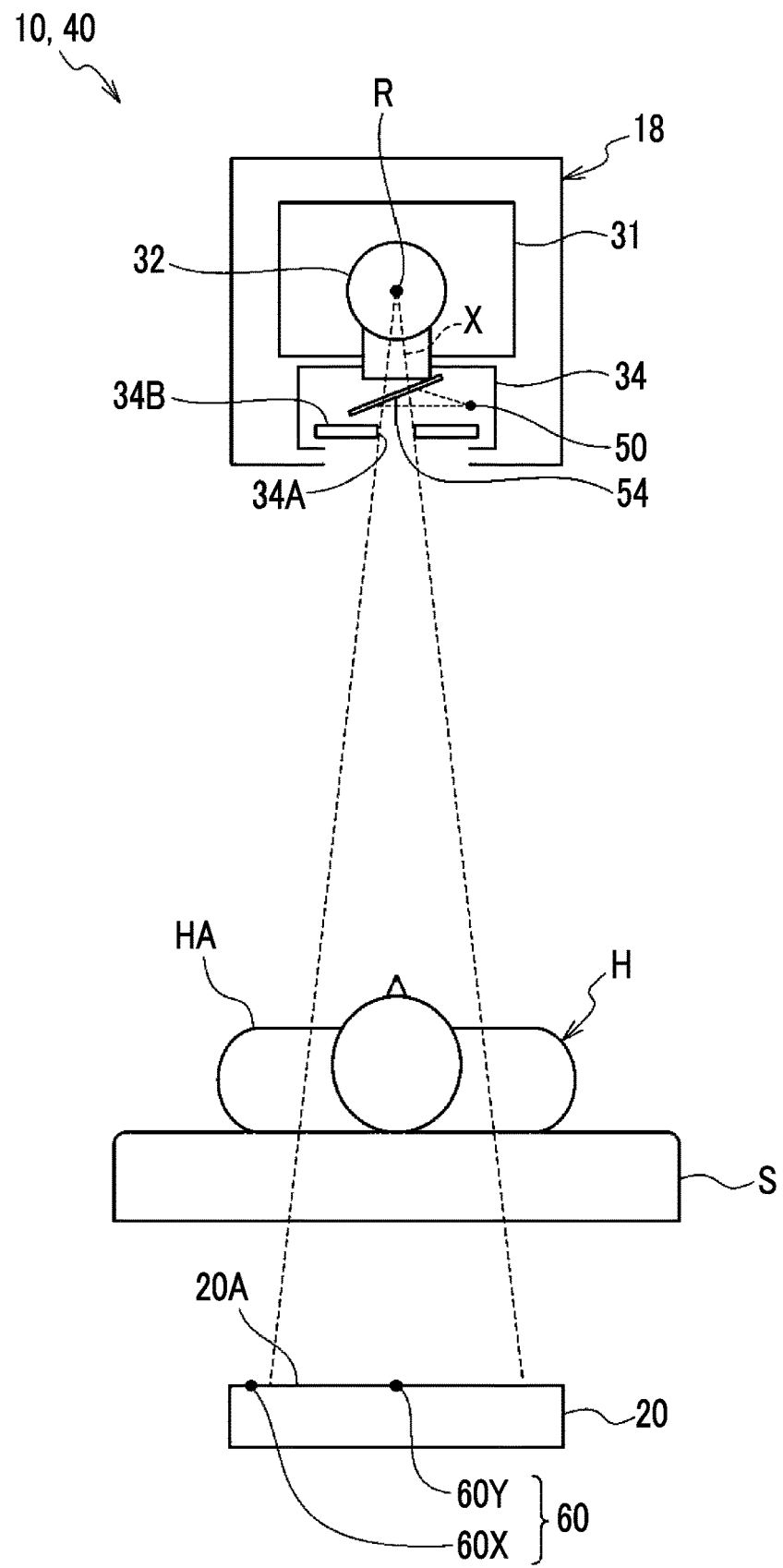
FIG. 4 is a cross-sectional view illustrating a state in which the radiography apparatus according to the first embodiment is used in an overtube posture.

Further, as illustrated in FIG. 4, the irradiation field limiter 34 is provided below the radiation source 31. The irradiation field limiter 34 (also referred to as a collimator or the like) has a rectangular irradiation opening 34A (see FIG. 1). The radiation generated by the radiation tube 32 is emitted to the subject H through the irradiation opening 34A. The irradiation field limiter 34 can adjust the opening area of the irradiation opening 34A. The irradiation field limiter 34 has, for example, four shielding plates 34B that shield radiation. In addition, in FIG. 4, among the four shielding plates 34B, only two shielding plates 34B that face each other in the X direction are illustrated. In each of the four shielding plates 34B, each side corresponds to each side of the irradiation opening 34A and defines the irradiation opening 34A. The position of the shielding plates 34B is changed to adjust the opening area of the irradiation opening 34A. As a result, the irradiation field of the radiation emitted from the irradiation unit 18 is changed.

Further, as illustrated in FIG. 1, the irradiation unit 18 can be rotated about an axis line of a rotation shaft 36 that extends in the width direction of the radiography apparatus 10 (the Y direction in FIG. 1) as a rotation center with respect to the arm 12.

The irradiation unit 18 is connected to, for example, the control device 28 and the power supply circuit (not illustrated) of the main body 16 illustrated in FIG. 1 by a cable (not illustrated) including a signal line for transmitting a control signal and a power line for supplying power.

Configuration of Image Receiving Unit

As illustrated in FIG. 1, the image receiving unit 20 is provided at the other end of the arm 12 which is a position facing the irradiation unit 18. The image receiving unit 20 comprises an image detector 20C (see FIG. 7) provided in a housing 20B. The image receiving unit 20 has an image receiving surface 20A that receives the radiation which has been emitted from the irradiation unit 18 and then transmitted through the subject H. The image receiving surface 20A is a surface on which the radiation carrying the information of the subject H is incident and is provided at a position corresponding to a detection surface of the image detector 20C.

The image detector 20C is, for example, a flat panel detector (FPD) of a digital radiography (DR) type. The FPD has a detection surface in which a plurality of pixels are two-dimensionally arranged and a thin film transistor (TFT) panel (not illustrated) for driving the pixels. Radiation is incident on the detection surface of the image detector 20C through the image receiving surface 20A. The image detector 20C converts the incident radiation into an electric signal and outputs a radiographic image indicating the subject H on the basis of the converted electric signal. For example, the image detector 20C is an indirect conversion type that converts radiation into visible light using a scintillator and converts the converted visible light into an electric signal. In addition, the image detector 20C may be a direct conversion type that directly converts radiation into an electric signal. Further, the image receiving unit 20 may have, for example, a configuration in which an image intensifier (I.I) and a camera are combined other than the configuration using the FPD.

Further, the image receiving unit 20 is connected to, for example, the control device 28 and the power supply circuit (not illustrated) of the main body 16 by a cable (not illustrated) including a signal line for transmitting a control signal and a power line for supplying power.

First Light Source

FIG. 4 schematically illustrates the arrangement of the irradiation unit 18, the subject H, the bed S, and the image receiving unit 20 in a case in which imaging is performed by the overtube method. As described above, in the overtube method, the radiation X is emitted to the subject H from the focus position R of the radiation tube 32 to capture a still image. In a case in which a still image is captured, the size of the irradiation opening 34A of the irradiation field limiter 34 is adjusted to change the irradiation field of the radiation emitted from the irradiation unit 18. Therefore, the irradiation field of the radiation X is adjusted according to the size of an imaging part.

The irradiation unit 18 is provided with a first light source 50 that emits visible light L indicating the irradiation field of the radiation X. The first light source 50 is provided inside the irradiation field limiter 34.

Figure 5:
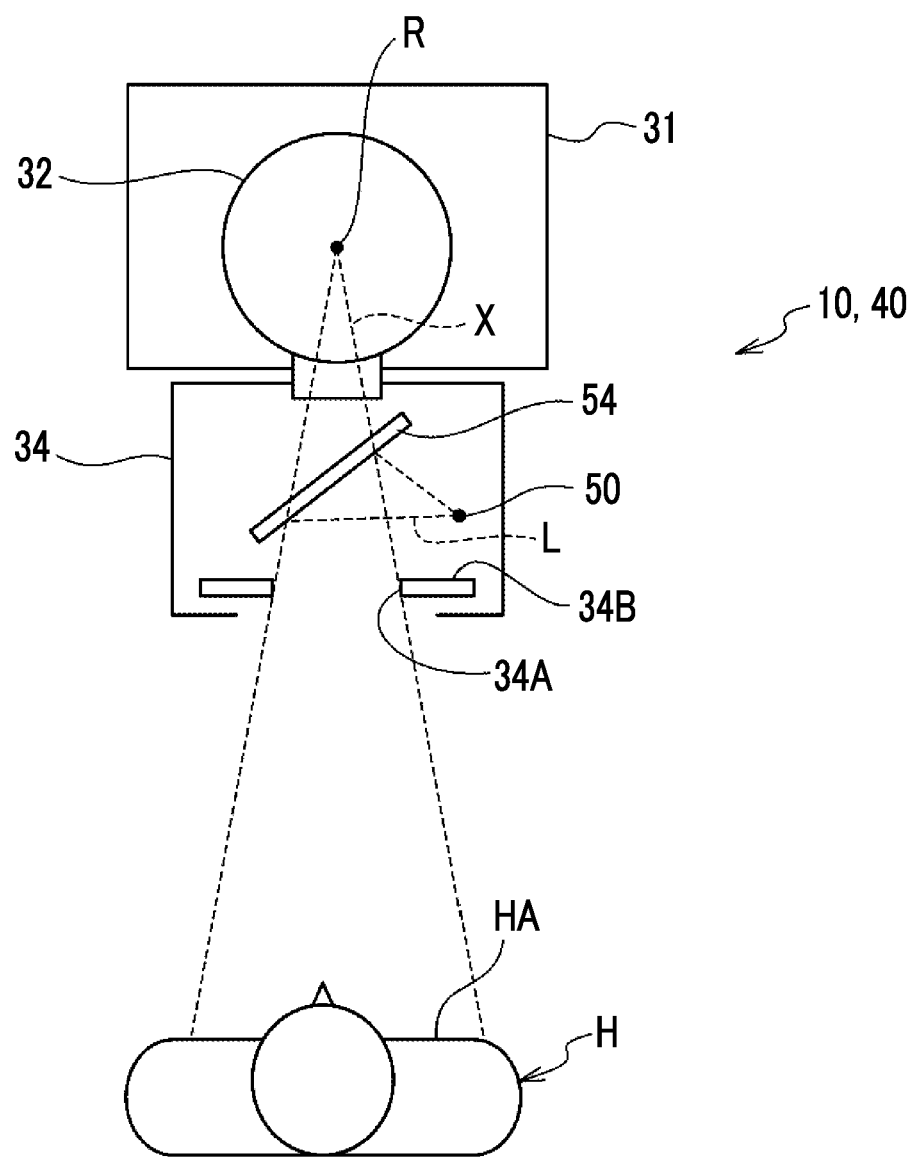
FIG. 5 is a cross-sectional view illustrating a first light source that is provided in an irradiation unit of the radiography apparatus according to the first embodiment.

As illustrated in FIG. 5, in the irradiation field limiter 34, an optical mirror 54 is disposed on an irradiation path through which the radiation X passes. The optical mirror 54 transmits the radiation X while reflecting the visible light L. The first light source 50 is disposed on the side of the optical mirror 54 so as to deviate from the irradiation path of the radiation X. The optical mirror 54 is inclined so as to reflect the visible light L emitted from the first light source 50 to the irradiation opening 34A on the irradiation path. Since the visible light L passes through the same irradiation opening 34A as the radiation X, the irradiation field is limited similarly to the radiation X. Therefore, the irradiation field of the visible light L and the irradiation field of the radiation X are matched with each other.

The visible light L passes through the irradiation opening 34A and reaches a surface HA of the subject H. Therefore, the irradiation field of the radiation X on the surface HA of the subject H is indicated by the visible light L. The first light source 50 is, for example, a white light emitting diode (LED).

Second Light Source

Figure 6:
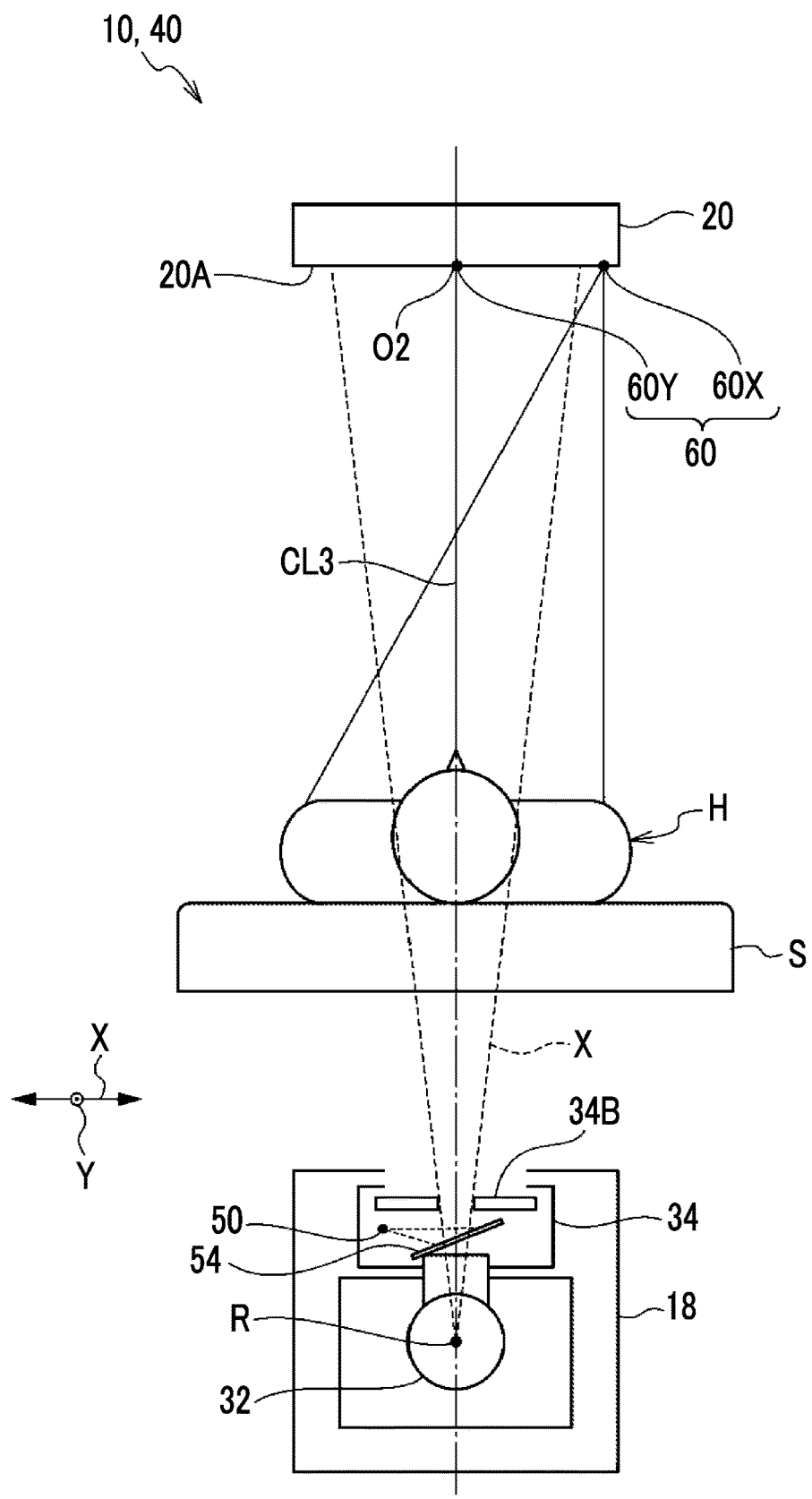
FIG. 6 is a cross-sectional view illustrating a state in which the radiography apparatus according to the first embodiment is used in an undertube posture.

FIG. 6 schematically illustrates the arrangement of the image receiving unit 20, the subject H, the bed S, and the irradiation unit 18 in a case in which imaging is performed by the undertube method. In the undertube method, the radiation X is emitted upward from the lower side of the subject H to capture a moving image. Even in a case in which a moving image is captured, the size of the irradiation opening 34A of the irradiation field limiter 34 is adjusted to change the irradiation field of the radiation emitted from the irradiation unit 18, as in the case in which a still image is captured. Therefore, the irradiation field of the radiation X is adjusted according to the size of an imaging part.

The irradiation unit 18 can continuously emit radiation in order to capture a moving image. The continuous emission of radiation includes so-called pulse emission in which radiation is repeatedly emitted at a preset short time interval for a short time, in addition to continuous emission in which radiation is continuously emitted.

The focus position R of the radiation tube 32 and a center position O2 of the image receiving surface 20A are disposed so as to be aligned with each other in the X-Y plane parallel to the image receiving surface 20A. Specifically, the radiation tube 32 is disposed such that the center position O2 of the image receiving surface 20A is located on an extension line CL3 of the focus position R in the Z direction.

Further, the focus position R of the radiation tube 32 and the center position of the irradiation opening 34A are disposed so as to be aligned with each other in the X-Y plane. Therefore, the center position of the irradiation field of the radiation X passing through the irradiation opening 34A and the position of the focus position R are aligned with each other in the X-Y plane.

The image receiving unit 20 is provided with second light sources 60X and 60Y that emit visible light indicating the center position of the irradiation field of the radiation X emitted by the irradiation unit 18. Specifically, the center position of the irradiation field of the radiation X indicated by the second light sources 60X and 60Y is the center position of the irradiation field of the radiation X on the surface HA of the subject H.

In the following description, in some cases, the second light source 60X and the second light source 60Y are generically referred to as a second light source 60.

Figure 7:
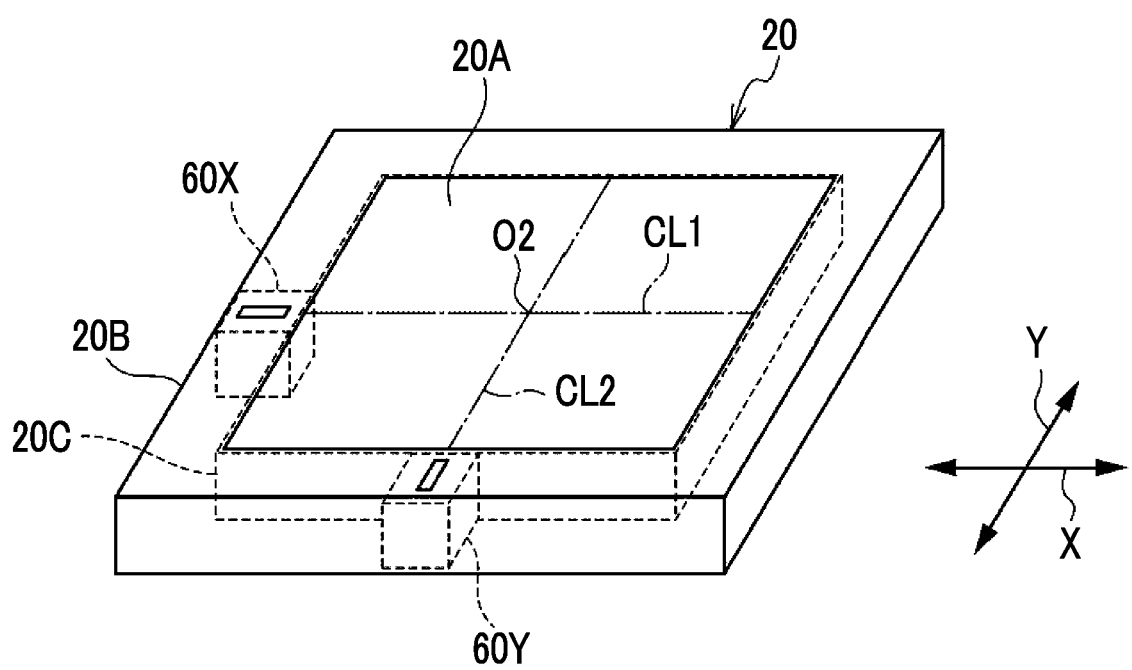
FIG. 7 is a cross-sectional view illustrating a second light source that is provided in an image receiving unit of the radiography apparatus according to the first embodiment.

As illustrated in FIG. 7, the second light source 60X and the second light source 60Y are provided in the housing 20B of the image receiving unit 20. The second light source 60X and the second light source 60Y are, for example, laser light sources. The second light source 60X and the second light source 60Y are disposed inside the housing 20B and outside the image detector 20C.

The second light source 60X is disposed on an extension line CL1 of the center position O2 of the image receiving surface 20A in the X direction. The second light source 60Y is disposed on an extension line CL2 of the center position O2 of the image receiving surface 20A in the Y direction.

Figure 8:
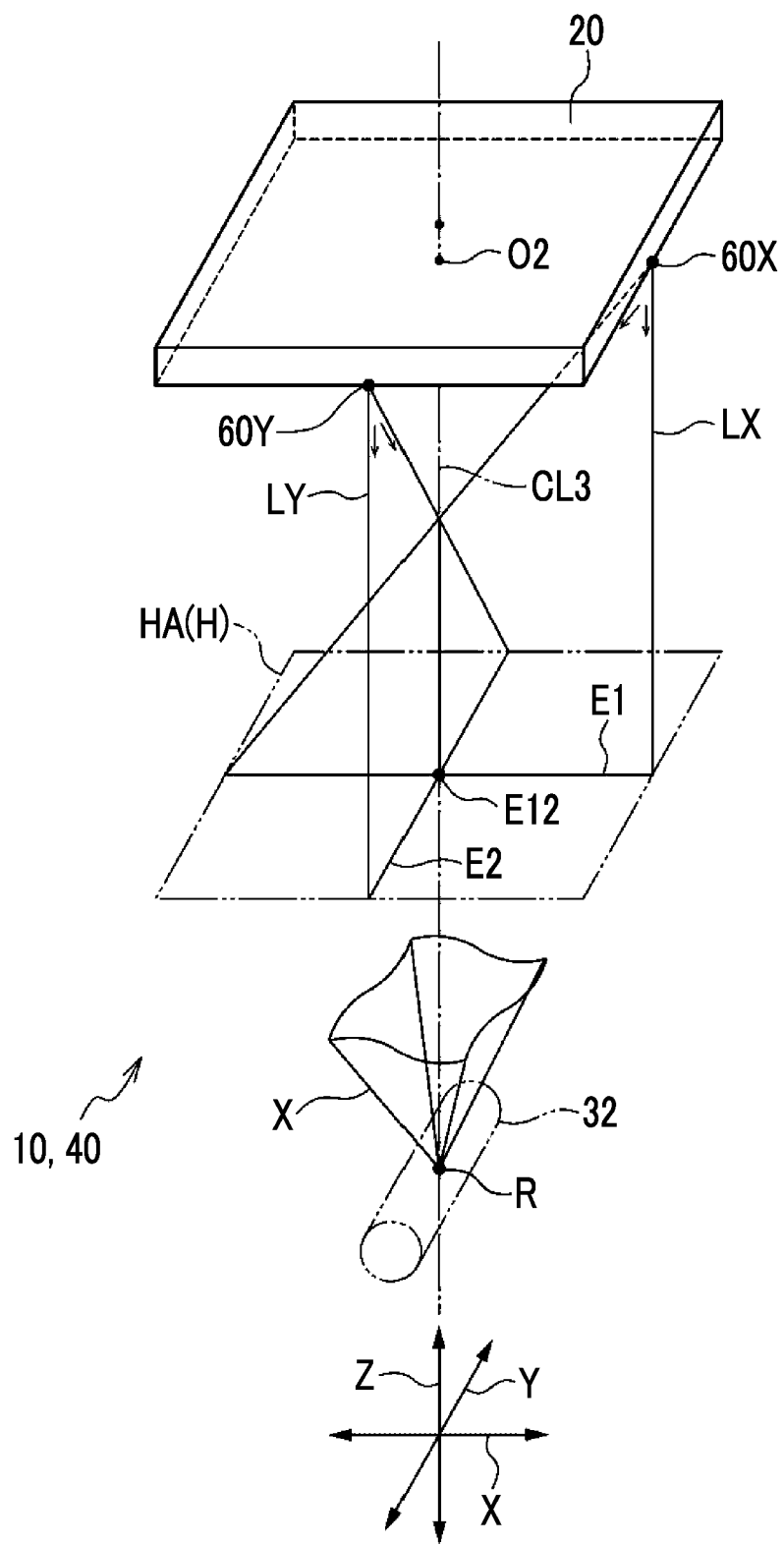
FIG. 8 is a cross-sectional view illustrating a state in which visible light is emitted from the second light source provided in the image receiving unit of the radiography apparatus according to the first embodiment.

As illustrated in FIG. 8, the visible light L emitted by the second light source 60X forms a beam LX which is diffused as it travels from a light emitting point in the Z direction. The beam LX is a planar beam with a triangular shape which has the light emitting point as a vertex in the X-Z plane along the X direction and the Z direction and linearly illuminates the surface HA of the subject H along the X direction in a plan view from the Z direction. A line E1 is a line that is formed on the surface HA by the beam LX.

Further, the visible light L emitted from the second light source 60Y forms a beam LY which is diffused as it travels from the light emitting point in the Z direction. The beam LY is a planar beam with a triangular shape which has the light emitting point as a vertex in the Y-Z plane along the Y direction and the Z direction and linearly illuminates the surface HA of the subject H along the Y direction in a plan view from the Z direction. A line E2 is a line that is formed on the surface HA by the beam LY.

The line E1 and the line E2 intersect with each other and an intersection point E12 is formed on the extension line of the center position O2 of the image receiving surface 20A in the Z direction. As described above, the second light source 60X and the second light source 60Y form a plurality of beams LX and beams LY intersecting each other on the surface HA. As described above, the center position O2 of the image receiving surface 20A is located on an extension line CL3 of the focus position R of the radiation tube 32 in the Z direction. Therefore, the intersection point E12 indicates the focus position R of the radiation on the surface HA of the subject H.

Figure 9:
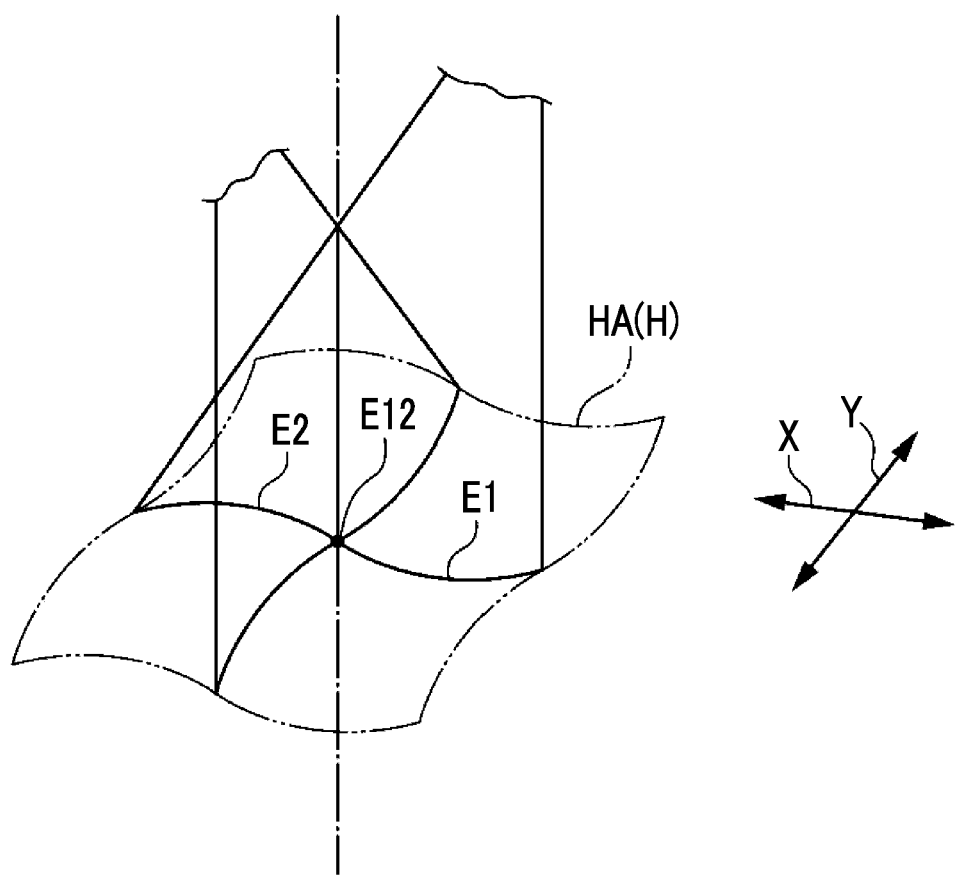
FIG. 9 is a cross-sectional view illustrating a state in which visible light is emitted to a subject having an uneven surface from the second light source provided in the image receiving unit of the radiography apparatus according to the first embodiment.

As illustrated in FIG. 9, in practice, the surface HA of the subject H is not a flat surface. For example, in a case in which the surface HA of the subject H is a body surface, the body surface is a curved surface and naturally has undulations. In a case in which the subject H is covered with a surgical drape, the surface HA is a surface of the surgical drape. The surface of the surgical drape is not flat. For example, wrinkles are formed on the surface in addition to the undulations following the shape of the body surface.

However, as illustrated in FIG. 8, the beam LX and the beam LY are planar beams with a triangular shape that has the light emitting point as a vertex in the Z-X plane and the Z-Y plane and linearly illuminate the surface HA along the X direction and the Y direction in a plan view from the Z direction, respectively. Therefore, as illustrated in FIG. 9, even in a case in which the surface HA is not a flat surface, the lines E1 and E2 formed on the surface HA extend in the X direction and the Y direction, respectively, while following the undulations of the surface HA. The intersection point E12 of the lines E1 and E2 corresponds to the center position of the irradiation field of the radiation X. As described above, the second light source 60X and the second light source 60Y are used to indicate the center position of the irradiation field of the radiation on the surface HA of the subject H, regardless of the shape of the surface HA of the subject H.

Functional Configuration of Radiography Apparatus

Figure 10:
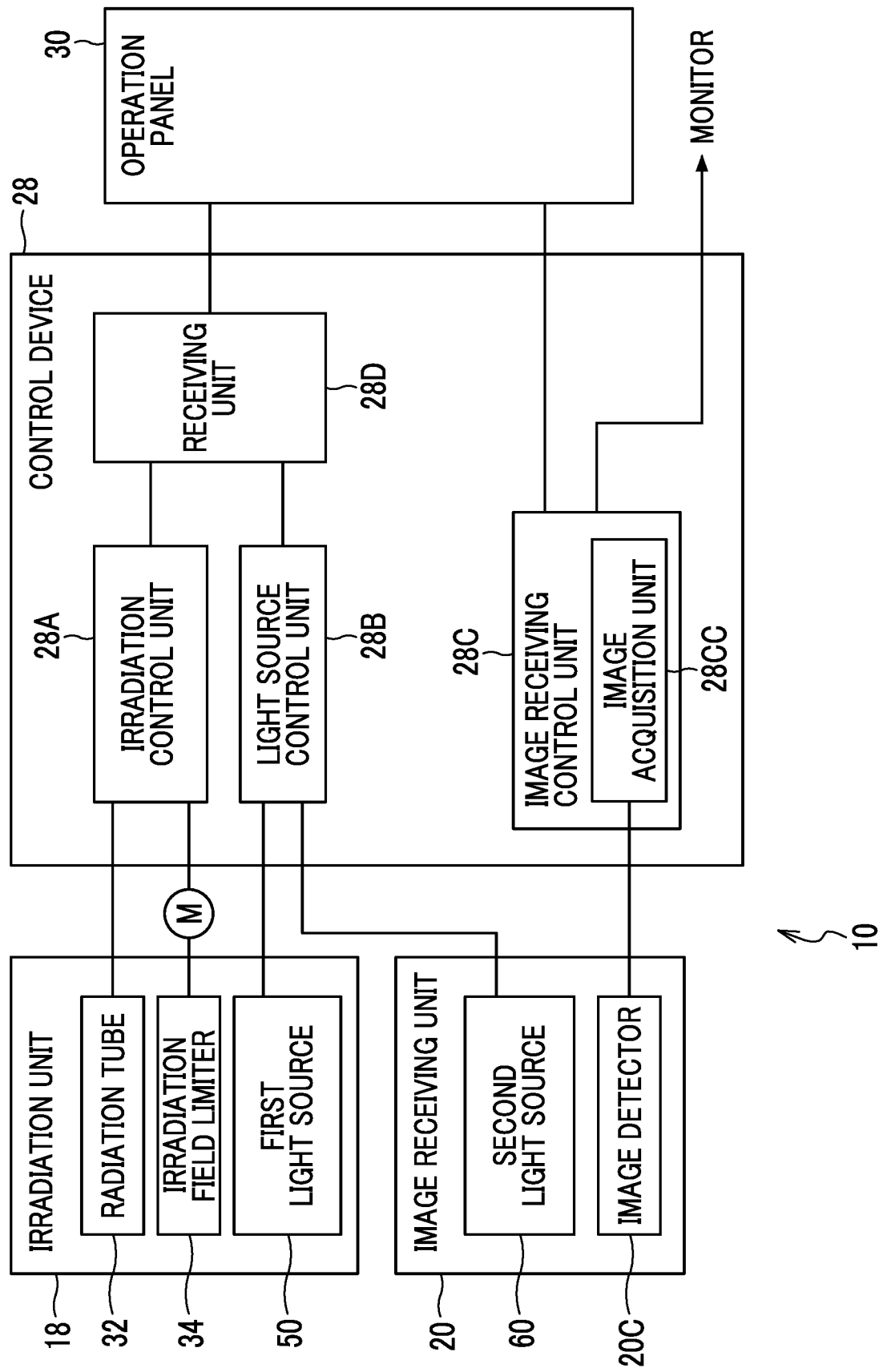
FIG. 10 is a block diagram illustrating a functional configuration of the radiography apparatus according to the first embodiment.

FIG. 10 is a block diagram mainly illustrating a functional configuration for controlling the first light source 50 and the second light sources 60X and 60Y among the functional configurations of the radiography apparatus 10. The radiography apparatus 10 comprises the control device 28. The control device 28 comprises an irradiation control unit 28A, a light source control unit 28B, and an image receiving control unit 28C.

The irradiation control unit 28A controls the emission of the radiation X by the irradiation unit 18. The image receiving control unit 28C controls the image detector of the image receiving unit 20. The irradiation control unit 28A and the image receiving control unit 28C perform control associated with the capture of a moving image and the capture of a still image in cooperation with each other.

In a case in which a moving image is captured, the irradiation control unit 28A directs the irradiation unit 18 to continuously emit the radiation X. The image receiving control unit 28C operates the image detector 20C of the image receiving unit 20 in synchronization with the irradiation operation of the irradiation unit 18. In a case in which a moving image is captured, basically, the irradiation time is not set as an imaging condition and commands to start and end the capture of the moving image are input through the operation panel 30. In a case in which an operation command is input from the operation panel 30 to the irradiation control unit 28A, the irradiation control unit 28A directs the irradiation unit 18 to start the emission of radiation under preset imaging conditions. Of course, the commands to start and end the capture of a moving image may be input by, for example, a foot switch other than the operation panel 30.

In the capture of a moving image, the image detector 20C repeats an image detection operation at a preset frame rate. The image output from the image detector 20C is transmitted to an image acquisition unit 28CC of the image receiving control unit 28C. The image receiving control unit 28C sequentially outputs the received images to a monitor (not illustrated). Then, the moving image of the subject H is displayed on the monitor.

Further, in a case in which a still image is captured, the irradiation control unit 28A directs the irradiation unit 18 to emit radiation X for a still image. In the capture of a still image, the irradiation control unit 28A operates the image detector 20C of the image receiving unit 20 in synchronization with the irradiation timing of the radiation X for a still image by the irradiation unit 18. A command to capture a still image is input through, for example, through an irradiation switch (not illustrated) connected to a receiving unit 28D. In the capture of a still image, the irradiation time is, for example, in the order of several tens of milliseconds to several hundreds of milliseconds. In a case in which a command to capture a still image is input to the irradiation control unit 28A through the receiving unit 28D, the irradiation control unit 28A operates the irradiation unit 18 under preset imaging conditions. In the capture of a still image, in a case in which the set irradiation time elapses, the irradiation operation of the irradiation unit 18 ends since the irradiation time is set in the imaging conditions.

In a case in which the irradiation operation ends, the image detector 20C starts to output the detected image. The image output from the image detector 20C is transmitted to an image acquisition unit 28CC of the image receiving control unit 28C. The image acquisition unit 28CC stores the data of the acquired still images in a memory (not illustrated). Then, the stored still image is displayed on the monitor (not illustrated). Therefore, the still image of the subject H is displayed on the monitor. Further, the still image may be displayed on the operation panel 30 in order to check the captured still image immediately after the image is captured.

The irradiation control unit 28A controls a motor M (see FIG. 10) that is connected to the shielding plate 34B of the irradiation field limiter 34 illustrated in FIG. 5 to adjust the size of the irradiation opening 34A. A command to adjust the irradiation opening 34A is input from the operation panel 30.

The light source control unit 28B controls the first light source 50 provided in the irradiation unit 18 and the second light source 60 provided in the image receiving unit 20 on the basis of a lighting command from the operation panel 30. The lighting command is input from the operation panel 30 to the light source control unit 28B through the receiving unit 28D. The light source control unit 28B turns on either the first light source 50 or the second light source 60 on the basis of a command to turn on the first light source 50 or the second light source 60.

Operation

The operation of the above-mentioned configuration will be described. In a case in which the radiography apparatus 10 is used to capture the still image of the subject H on the bed S, for example, the overtube method illustrated in FIG. 4 is used. Specifically, the operator sets the arm 12 in the overtube posture in which the irradiation unit 18 is disposed above the subject H and the image receiving unit 20 is disposed below the subject H. In the capture of a still image, the operator operates the operation panel 30 to turn on the first light source 50. In a case in which the first light source 50 is turned on, the visible light L is emitted from the first light source 50 to the subject H through the irradiation opening 34A. In a case in which the size of the irradiation opening 34A is adjusted, the size of the irradiation field of the visible light L is also changed according to the size of the irradiation opening 34A.

Since the irradiation opening 34A is an opening through which the radiation X is emitted, the irradiation field of the radiation X is indicated by the visible light L of the first light source 50. Therefore, the operator can check the irradiation field of the radiation X using the visible light L. The operator adjusts the relative positional relationship between the arm 12 and the subject H, and the irradiation opening 34A while checking the irradiation field indicated by the visible light L, thereby adjusting the irradiation field in the capture of a still image. After the adjustment of the irradiation field ends, a still image is captured using the radiation X. Since the irradiation field is set to an appropriate position and size, an appropriate radiographic image indicating the desired imaging part can be obtained.

Further, in a case in which the moving image of the subject H on the bed S is captured using the radiography apparatus 10, for example, the undertube method illustrated in FIG. 6 is used. Specifically, the operator sets the arm 12 to the undertube posture in which the irradiation unit 18 is disposed below the subject H and the image receiving unit 20 is disposed above the subject H. The moving image is captured during surgery. Before surgery is started, the operator sets the irradiation field of the radiation X in the capture of the moving image of a treatment target part. In the capture of a moving image, the operator operates the operation panel 30 to turn on the second light source 60X and the second light source 60Y.

In a case in which the second light sources 60X and 60Y are turned on, the beam LX and the beam LY illustrated in FIG. 8 are formed by the visible light L emitted from the second light sources 60X and 60Y, respectively. The beam LX and the beam LY linearly illuminate the surface HA of the subject H along the X direction and the Y direction, respectively. Therefore, the line E1 and the line E2 are formed on the surface HA. The line E1 and the line E2 intersect each other and the intersection point E12 indicates the center position of the irradiation field of the radiation X.

The operator checks the position of the intersection point E12 to check whether or not the center position of the irradiation field of the radiation X is aligned with the center position of the treatment target part. In a case in which the positions deviate from each other, the position of the arm 12 is adjusted. After the adjustment of the center position of the irradiation field and the center position of the treatment target part ends, the size of the irradiation opening 34A is adjusted as necessary to adjust the size of the irradiation field. Even in a case in which the size of the irradiation field is reduced, the center position of the treatment target part does not deviate from the irradiation field since the center position of the irradiation field is aligned with the center position of the treatment target part.

After the adjustment of the irradiation field ends, surgery is started and a moving image is captured using the radiation X in parallel to the surgery. Since the center position of the irradiation field of the radiation X is aligned with the center position of the treatment target part, the center position of the treatment target part is displayed at the center position of a screen of the monitor on which the moving image is displayed. Therefore, the doctor can perform surgery while checking the state of the treatment target part on the monitor.

Effect

As described above, according to the radiography apparatus 10 of the first embodiment, the arm 12 is rotated to reverse the positional relationship between the image receiving unit 20 and the irradiation unit 18 that face each other with the subject H interposed therebetween (see FIGS. 3A to 3C). Therefore, images can be captured by the overtube method illustrated in FIG. 4 and the undertube method illustrated in FIG. 6.

As illustrated in FIG. 5, the irradiation unit 18 is provided with the first light source 50 that indicates the irradiation field of the radiation X. Therefore, in a case in which a still image is captured by the overtube method, the irradiation field can be checked by the visible light L before imaging using the radiation X. Therefore, it is possible to obtain a still image (radiographic image) in which the irradiation field is set in an appropriate range, without using the unnecessary radiation X that does not contribute to the formation of the radiographic image.

Further, as illustrated in FIG. 8, the image receiving unit 20 comprises the second light source 60 that emits visible light indicating the center position of the irradiation field of the radiation X emitted by the irradiation unit 18. Therefore, even in a case in which a moving image is captured by the undertube method, it is easy to understand the center position of the irradiation field before the radiation X is emitted, as compared to the related art in which visible light indicating the periphery of the irradiation field is emitted.

For example, the area of the treatment target part may be very small in a case in which a treatment to puncture the treatment target part with a needle or a treatment to insert a thin tube, such as a catheter, is performed as surgery.

In this case, it is difficult to understand the center position of the irradiation field at a glance in the method according to the related art in which the periphery of the irradiation field is linearly indicated by laser light. In particular, in a case in which the area of the treatment target part is very small with respect to the area of the irradiation field whose periphery is linearly indicated, the distance between the periphery of the irradiation field and the center position of the irradiation field is long. Therefore, it is difficult to estimate the center position from the periphery and to align the center position of the irradiation field with the center position of the treatment target part. In a case in which the center position of the irradiation field is not aligned with the center position of the treatment target part and the size of the irradiation opening is adjusted to narrow the irradiation field, there is a concern that the treatment target part will deviate from the irradiation field.

In contrast, according to the technology of the present disclosure, since the second light source 60 can indicate the center position of the irradiation field, it is easy to understand the center position of the irradiation field as compared to the related art. As a result, it is easy to align the center position of the irradiation field with the center position of the treatment target part. Further, in a case in which the center position of the irradiation field is aligned with the center position of the treatment target part, the center position of the treatment target part is less likely to deviate from the irradiation field even though the size of the irradiation opening 34A is adjusted. As described above, according to the technology of the present disclosure, advantageous effects can be obtained as compared to the related art.

Further, in the radiography apparatus 10 according to this example, the irradiation unit 18 can continuously emit radiation in order to capture a moving image. In many cases, a moving image of the treatment target part is captured during surgery. In this case, as described above, it is important to align the center position of the irradiation field with the center position of the treatment target part. The technology of the present disclosure is particularly effective for the radiography apparatus 10 that can capture moving images. In some cases, it is necessary to indicate the center position of the irradiation field even in the capture of still images. Therefore, the technology of the present disclosure may be applied to the radiography apparatus 10 that can only capture still images.

In the radiography apparatus 10 according to this example, the second light source 60 is a laser light source. The laser light sources have a narrower divergence angle and higher directivity than other light sources such as LED light sources and halogen lamps. Therefore, it is easy to emit light that indicates one point and light that linearly illuminates the surface HA. Therefore, it is preferable to use a laser light source as the second light source that emits visible light indicating the center position of the irradiation field.

In addition, the second light source 60 according to this example forms a plurality of beams that linearly illuminates the surface HA of the subject H as illustrated in FIG. 8 and intersect each other on the surface HA to indicate the center position of the irradiation field of the radiation X at the intersection point E12 of the plurality of beams. Therefore, it is easy for the operator of the radiography apparatus 10 to visually recognize the center position of the irradiation field. Further, the beams are particularly effective in a case in which the surface HA of the subject H has undulations as illustrated in FIG. 9.

In the radiography apparatus 10 according to this example, the first light source 50 is an LED light source. The LED light source can be downsized as compared to, for example, a halogen lamp. Further, since the LED light source has a larger divergence angle than the laser light source, the LED light source is advantageous in a case in which it illuminates the entire region of the irradiation field. Therefore, it is preferable to use the LED light source as the first light source that emits visible light indicating the irradiation field.

In this embodiment, the two lines E1 and E2 are formed on the surface HA by the beams LX and LY emitted by the two second light sources 60X and 60Y, respectively. However, three or more second light sources 60 may be provided. For example, three or more second light sources 60 may be used and the center position of the irradiation field of radiation may be indicated by the intersection point of three or more lines formed by three or more beams emitted by the three or more second light sources.

Second Embodiment

Next, a radiography apparatus 40 according to a second embodiment of the present disclosure will be described with reference to FIG. 11. Since the main configuration of the radiography apparatus 40 is the same as that of the radiography apparatus 10 according to the first embodiment illustrated in FIGS. 1 to 10, the description thereof will not be repeated. The difference will be mainly described below.

Functional Configuration of Radiography Apparatus

Figure 11:
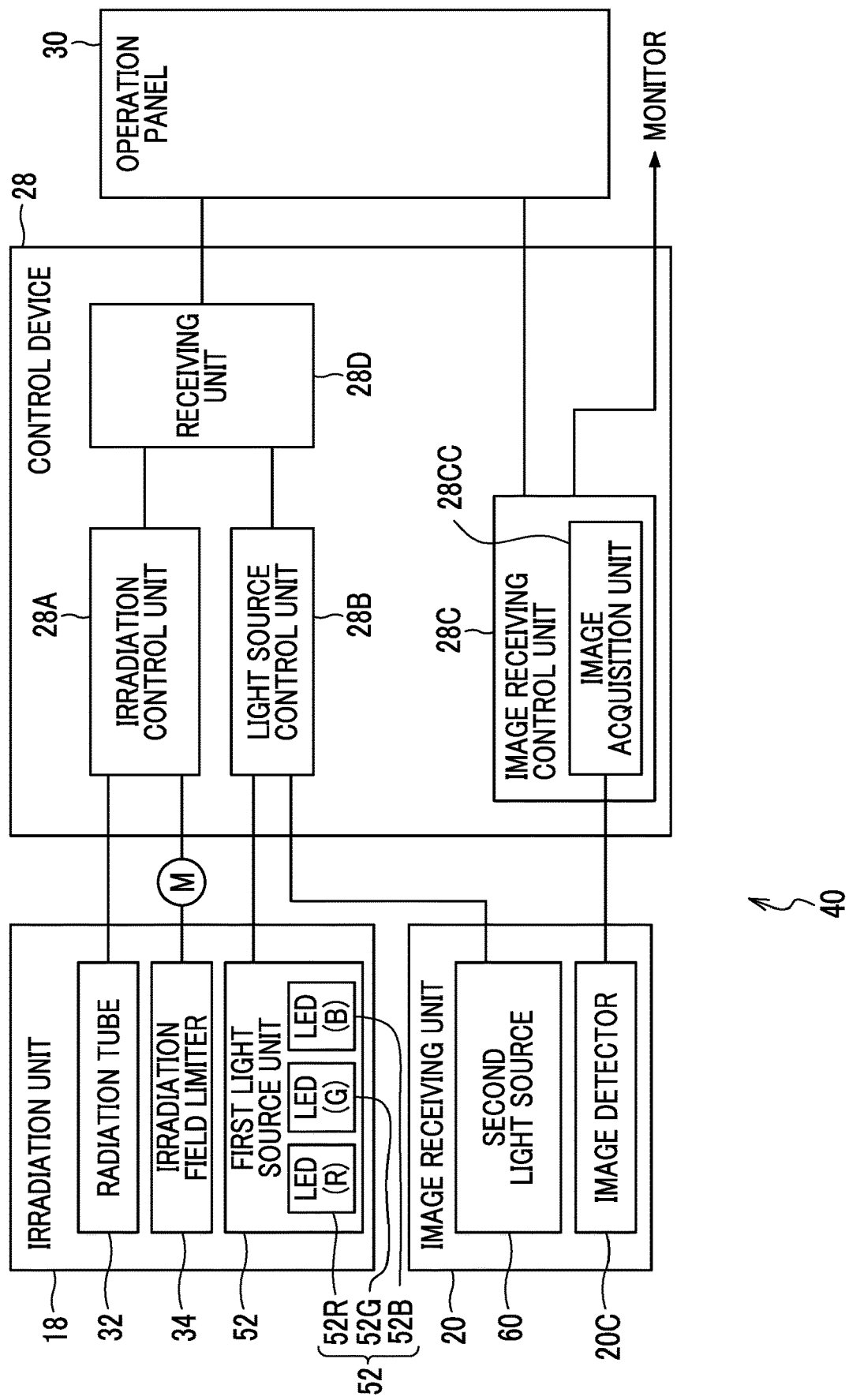
FIG. 11 is a block diagram illustrating a functional configuration of a radiography apparatus according to a second embodiment.

As illustrated in FIG. 11, the radiography apparatus 40 includes a first light source unit 52. The first light source unit 52 is an example of a color-variable light source that can change the color of emitted light. The first light source unit 52 comprises three light emitting elements, that is, a red LED element 52R, a green LED element 52G, and a blue LED element 52B, as a plurality of light emitting elements that emit light components of different colors.

In the radiography apparatus 40, the light source control unit 28B changes the color of the light emitted by the light source unit 52 as a color-variable light source. Further, the light source control unit 28B adjusts the amount of light of the light source unit 52. Specifically, the light source control unit 28B adjusts the amount of light of each of the red LED element 52R, the green LED element 52G, and the blue LED element 52B.

The light source control unit 28B can selectively turn on the red LED element 52R, the green LED element 52G, and the blue LED element 52B to change the color of light to any of red, green, and blue. Further, white light is generated in a case in which the red LED element 52R, the green LED element 52G, and the blue LED element 52B are turned on to emit light at the same ratio. In addition, the ratio of the amounts of light of the red LED element 52R, the green LED element 52G, and the blue LED element 52B is adjusted to generate light components of various colors. The light source controller 28B adjusts the ratio of the amounts of light of the red LED element 52R, the green LED element 52G, and the blue LED element 52B to change the color of the light emitted by the first light source unit 52.

In addition, in a state in which the red LED element 52R, the green LED element 52G, and the blue LED element 52B are selectively turned on, the light source control unit 28B changes the amount of light of the turned-on LED element to adjust the amount of light. Further, in a case in which all of the red LED element 52R, the green LED element 52G, and the blue LED element 52B are turned on, the light source control unit 28B adjusts the amounts of light at the same ratio, thereby adjusting only the amount of light without changing colors.

As described above, the light source control unit 28B is an example of a color adjustment unit that adjusts the color of light emitted from the color-variable light source and a light amount adjustment unit that adjusts the amount of light of the first light source. The change of the color and the adjustment of the amount of light are performed in response to an operation command from the operation panel 30.

Operation and Effect

According to the radiography apparatus 40 of the second embodiment, it is possible to change the color of the first light source unit 52 as the first light source. The change of the color makes it possible to change the color of the visible light L indicating the irradiation field to a color that is highly visible to the operator. For example, in a case in which the subject H is a person, the body surface has a flesh color. Therefore, the visibility can be improved by setting the visible light L to a color (for example, green) that is easily distinguishable from the human body.

The first light source unit 52 which is an example of the color-variable light source includes a plurality of light emitting elements (the red LED element 52R, the green LED element 52G, and the blue LED element 52B) that emit light components of different colors. Therefore, the number of colors that can be changed is larger than that in a case in which only a single-color light emitting element is provided. Therefore, the choices of colors that can be selected according to the type of subject and the environment are widened.

The irradiation control unit 28A which is an example of the light amount adjustment unit adjusts the amount of light of the first light source unit 52 which is an example of the first light source. This makes it possible to adjust the amount of light to an appropriate value.

The first light source unit 52 in this embodiment comprises the red LED element 52R, the green LED element 52G, and the blue LED element 52B. However, the embodiment of the disclosure is not limited thereto.

The number of light emitting elements in the first light source unit 52 as the color-variable light source is not limited to three and the first light source unit 52 may have two or more light emitting elements that emit light components of different colors. The type of light source is not limited to the LED. For example, a halogen lamp or a fluorescent tube may be used. Further, the number of light emitting elements in the color-variable light source may be one. For example, even in a case in which one light emitting element is provided, the light emitting element and phosphors that emit fluorescent light components of different colors, using the light emitted by the light emitting element as excitation light, may be combined to generate a plurality of colors.

In this example, the light source control unit 28B adjusts the color of light and the amount of light of the first light source unit 52. However, the light source control unit 28B may adjust at least one of the color of light or the amount of light. In a case in which at least one of the color of light or the amount of light can be adjusted, the effect of adjusting the visibility of visible light can be obtained.

In addition, the light source control unit 28B may adjust at least one of the color of light or the amount of light of the second light source 60. The adjustment of the light of the second light source 60 makes it possible to appropriately adjust the color and amount of visible light L indicating the center position of the irradiation field according to, for example, the subject H and the environment.

Further, the light source control unit 28B may control at least one of the first light source unit 52 or the second light source 60 and may not control both the first light source unit 52 and the second light source 60.

Third Embodiment

Figure 12:
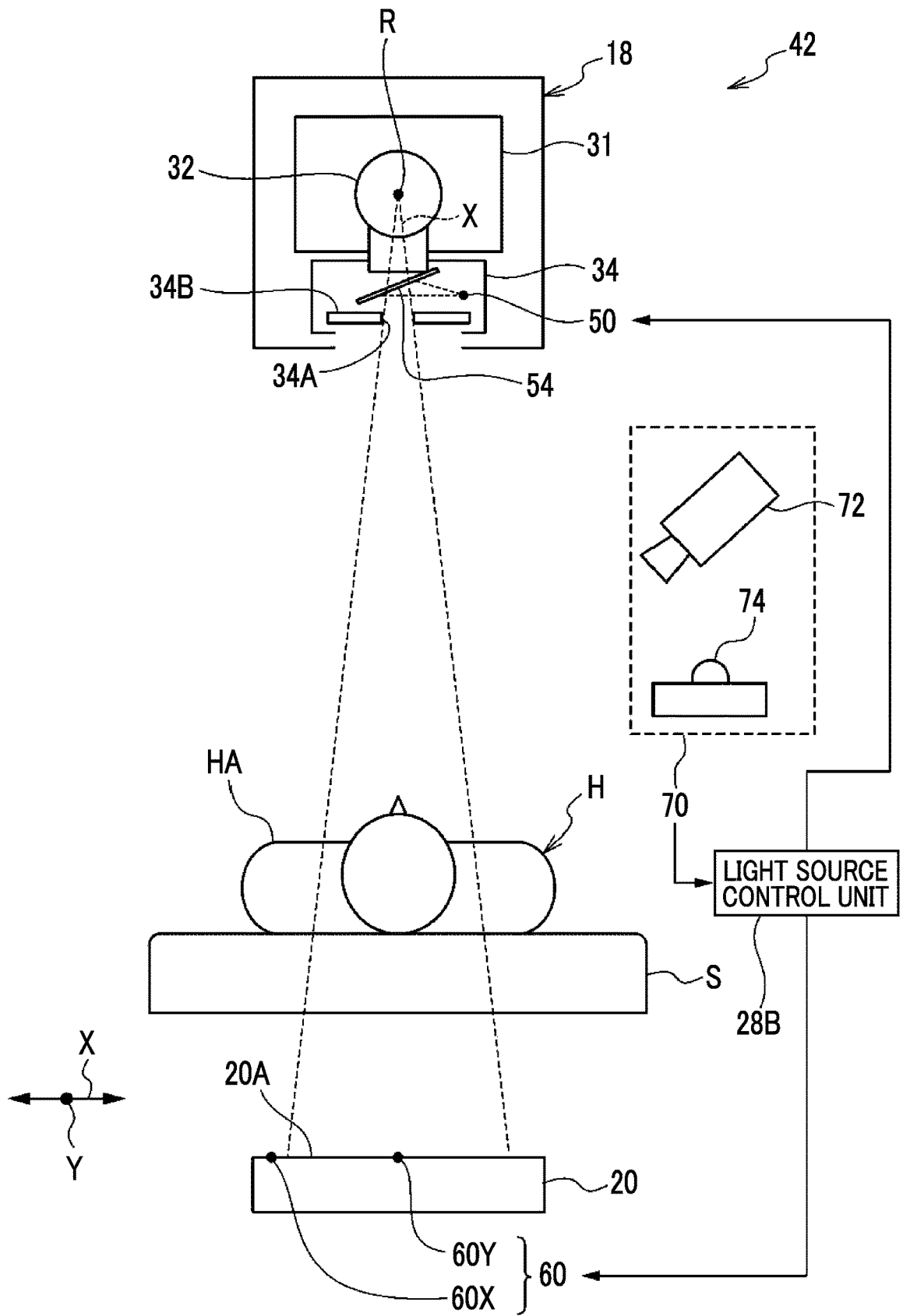
FIG. 12 is a cross-sectional view illustrating a state in which a radiography apparatus according to a third embodiment is used in the overtube posture.

Next, a radiography apparatus 42 according to a third embodiment of the present disclosure will be described with reference to FIG. 12. The main configuration of the radiography apparatus 42 is the same as that of the radiography apparatus 10 according to the first embodiment illustrated in FIGS. 1 to 10 except that the radiography apparatus 42 includes an optical sensor 70 as illustrated in FIG. 12. The optical sensor 70 comprises a color sensor 72 and an illuminance sensor 74.

The color sensor 72 is an example of a color sensor that detects the color of the subject H (the color of the surface HA) and the illuminance sensor 74 is an example of an illuminance sensor that detects environmental illuminance. The color sensor 72 has, for example, a color image sensor and an image processing unit in order to detect the color of the subject H. For example, a color image sensor obtained by combining an image sensor, such as a charge coupled device (CCD) image sensor or a complementary metal oxide semiconductor (CMOS) image sensor in which an imaging surface is formed by a plurality of pixels, and micro color filters that are arranged so as to corresponding to each pixel is used as the color image sensor. The color sensor 72 is disposed so as to capture an image of the surface HA of the subject H using the color image sensor and to acquire a color image of the surface HA.

The image processing unit of the color sensor 72 analyzes the color image to detect the color of the surface HA. The color sensor 72 transmits the detected color of the surface HA to the light source control unit 28B.

The illuminance sensor 74 detects environmental illuminance which is the illuminance of environment inside the room in which the radiography apparatus 42 is installed. The "environmental illuminance" is the illuminance of environmental light that illuminates the surface HA of the subject H. Examples of the "environmental light" include light emitted from a lighting device or the like that illuminates the room in which the radiography apparatus 42 is installed and light emitted from a shadowless lamp that is provided in the operating room. The illuminance sensor 74 transmits the detected illuminance to the light source control unit 28B.

The light source control unit 28B changes the color of the color-variable light source (at least one of the first light source 50 or the second light source 60) according to the color of the subject H detected by the color sensor 72. Further, the light source control unit 28B adjusts the amount of light of at least one of the first light source 50 or the second light source 60 which indicates the irradiation field according to the illuminance detected by the illuminance sensor 74.

Specifically, similarly to the second embodiment, the light source control unit 28B changes the color of the visible light L of the color-variable light source to a color that is easily distinguishable from the color of the surface HA of the subject H. Therefore, it is possible to improve the visibility of the visible light L. Further, the light source control unit 28B adjusts the amount of light of the color-variable light source according to the environmental illuminance such that the illuminance of the visible light L increases in a case in which the environmental illuminance is high.

As described above, in the radiography apparatus 42 according to the third embodiment, the light source control unit 28B which is an example of the color adjustment unit adjusts the color of light according to the color of the surface HA of the subject H detected by the color sensor 72. In the third embodiment, the color sensor 72 and the illuminance sensor 74 are used unlike the second embodiment. Therefore, the color and amount of light can be changed more easily than that in the second embodiment.

In the third embodiment, the example in which both the color sensor 72 and the illuminance sensor 74 are used to adjust both the color and the amount of light has been described. However, both the color and the amount of light may not be necessarily adjusted. For example, at least one of the color sensor 72 or the illuminance sensor 74 may be used to adjust at least one of the color or the amount of light.

In each of the above-described embodiments, the LED light source has been described as an example of the first light source 50 and the laser light source has been described as an example of the second light source 60. However, the types of light sources are not limited thereto. For example, a halogen lamp may be used as the first light source 50 and an LED light source may be used as the second light source 60. Of course, as described above, it is preferable that the LED light source is used as the first light source 50 and the laser light source is used as the second light source 60.

Further, the light source that forms a beam linearly illuminating the surface HA of the subject H has been described an example of the second light source 60. However, a light source may be used which emits spot light indicating the center position of the irradiation field in a dot shape. Of course, the use of the light source that forms a beam linearly illuminating the surface HA of the subject H as the second light source 60 as described above makes it possible to accurately indicate the center position of the irradiation field even in a case in which the surface HA has undulations as illustrated in FIG. 9. Therefore, it is preferable to use the laser light source described in the above-described embodiments as the second light source 60.

In each of the above-described embodiments, the C-arm having a C-shape in a side view has been described as an example of the arm 12. However, a U-arm having a U-shape in a side view may be used. Similarly to the C-arm, the U-arm can hold, for example, the irradiation unit 18 and the image receiving unit 20 in a posture in which they face each other.

In the above-described embodiments, the image receiving unit 20 may be attached to the arm 12 so as not to be detachable or may be attached to the arm 12 so as to be detachable. Further, the image receiving unit 20 may be configured by an image detector and an accommodation portion that attachably and detachably accommodates the image detector such that only the image detector is removed with the accommodation portion attached to the arm 12. In this case, the accommodation portion may not be attachable to and detachable from the arm 12 or may be attachable to and detachable from the arm 12. This configuration in which at least the image detector is attachable to and detachable from the arm 12 makes it possible to selectively use, for example, the image detectors having different screen sizes.

In addition, X-rays have been described as an example of the radiation. However, the present disclosure is not limited to the X-rays. For example, y-rays may be used.

In each of the above-described embodiments, for example, the following various processors can be used as a hardware structure of processing units performing various processes, such as the irradiation control unit 28A, the light source control unit 28B, and the image receiving control unit 28C. The various processors include, for example, a CPU which is a general-purpose processor executing software to function as various processing units as described above, a programmable logic device (PLD), such as a field programmable gate array (FPGA), which is a processor whose circuit configuration can be changed after manufacture, and a dedicated electric circuit, such as an application-specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs and/or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as the hardware structure.

Furthermore, specifically, an electric circuit (circuitry) obtained by combining circuit elements, such as semiconductor elements, can be used as the hardware structure of the various processors.

What is claimed is:

1. A radiography apparatus comprising:
an irradiation unit that emits radiation;
an arm to which the irradiation unit and an image receiving unit that receives the radiation are capable of being attached at a position where the irradiation unit and the image receiving unit face each other with a subject interposed therebetween and which is rotated to reverse a positional relationship between the irradiation unit and the image receiving unit with respect to the subject;
a first light source that is provided in the irradiation unit and emits visible light indicating an irradiation field of the radiation; and
a second light source that is provided in the image receiving unit and emits visible light indicating a center position of the irradiation field of the radiation emitted by the irradiation unit.

2. The radiography apparatus according to claim 1, wherein the irradiation unit is capable of continuously emitting the radiation to capture a moving image.

3. The radiography apparatus according to claim 1, wherein the second light source is a laser light source.

4. The radiography apparatus according to claim 1, wherein the second light source forms, as the visible light, a plurality of beams that linearly illuminate a surface of the subject and intersect each other on the surface, and the center position of the irradiation field is capable of being indicated by an intersection point of the plurality of beams.

5. The radiography apparatus according to claim 1, wherein the first light source is an LED light source.

6. The radiography apparatus according to claim 1, wherein at least one of the first light source or the second light source is a color-variable light source that is capable of changing a color.

7. The radiography apparatus according to claim 6, wherein the color-variable light source has a plurality of light emitting elements that emit light components of different colors.

8. The radiography apparatus according to claim 6, further comprising:
a color sensor that detects a color of the subject; and
a color adjustment unit that adjusts a color of the light emitted by the color-variable light source according to the color detected by the color sensor.

9. The radiography apparatus according to claim 1, further comprising:
a light amount adjustment unit that adjusts an amount of light of at least one of the first light source or the second light source.

10. The radiography apparatus according to claim 9, further comprising:
an illuminance sensor that detects environmental illuminance,
wherein the light amount adjustment unit adjusts an amount of visible light indicating the irradiation field according to the illuminance detected by the illuminance sensor.

* * * * *